(12) United States Patent
Huang et al.

(10) Patent No.: US 8,022,703 B1
(45) Date of Patent: Sep. 20, 2011

(54) METHOD FOR RAPID DETECTING TUMOR

(76) Inventors: Kai-Wen Huang, Taipei (TW);
Shieh-Yueh Yang, Taipei County (TW);
Hong-Chang Yang, Taipei County
(TW); Herng-Er Horng, Taipei County
(TW)

( * ) Notice: Subject to any disclaimer, the term of this patent is extended or adjusted under 35 U.S.C. 154(b) by 7 days.

(21) Appl. No.: 12/775,198

(22) Filed: May 6, 2010

(51) Int. Cl.
*G01V 3/00* (2006.01)
(52) U.S. Cl. ...................................... 324/309
(58) Field of Classification Search ......... 324/300–322; 600/407, 410, 421, 422
See application file for complete search history.

(56) References Cited

U.S. PATENT DOCUMENTS

| | | |
|---|---|---|
| 3,789,832 A | 2/1974 | Damadian |
| 4,608,991 A | 9/1986 | Rollwitz |
| 6,121,775 A | 9/2000 | Pearlman |
| 7,053,610 B2 * | 5/2006 | Clarke et al. .................. 324/300 |
| 7,116,102 B2 * | 10/2006 | Clarke et al. .................. 324/300 |
| 7,148,684 B2 * | 12/2006 | Laubacher et al. ........... 324/300 |
| 7,248,044 B2 * | 7/2007 | Kobayashi et al. ........... 324/248 |
| 7,265,550 B2 * | 9/2007 | Laubacher et al. ........... 324/318 |
| 7,279,897 B2 * | 10/2007 | Alvarez et al. ................ 324/310 |
| 7,521,932 B2 * | 4/2009 | Carter et al. .................. 324/318 |
| 2008/0187200 A1 | 8/2008 | Degani et al. |
| 2009/0028405 A1 | 1/2009 | Degani et al. |
| 2010/0327869 A1 * | 12/2010 | Kim et al. ..................... 324/309 |

FOREIGN PATENT DOCUMENTS

| WO | 2008/147921 A1 | 4/2008 |
|---|---|---|
| WO | 2008/093999 A1 | 7/2008 |

* cited by examiner

*Primary Examiner* — Brij Shrivastav
(74) *Attorney, Agent, or Firm* — WPAT, P.C.; Anthony King

(57) ABSTRACT

The present invention provides a method for rapid detecting tumor. Moreover, this invention uses only the $T_1^{-1}$ value as a parameter to distinguish tumor from normal tissue, and the accuracy of this detection is highly reliable.

20 Claims, 14 Drawing Sheets

METHOD FOR RAPID DETECTING TUMOR

FIELD OF THE INVENTION

The present invention relates to a method for rapid detecting tumor using a tabletop low-field nuclear magnetic resonance (NMR) system.

BACKGROUND OF THE INVENTION

Nuclear magnetic resonance (NMR) is the name given to a physical resonance phenomenon involving the observation of specific quantum mechanical magnetic properties of an atomic nucleus in the presence of an applied, external magnetic field. Many scientific techniques exploit NMR phenomena to study molecular physics, crystals and non-crystalline materials through NMR spectroscopy. NMR is also routinely used in advanced medical imaging techniques, such as in magnetic resonance imaging (MRI).

A superconducting quantum interference device (SQUID) is a sensitive detector which is used to measure extremely weak magnetic signals, such as subtle changes in the human body's electromagnetic energy field based on the quantum mechanical Josephson effect. A Josephson junction is made up of two superconductors, separated by an insulating layer so thin that superconducting electrons can tunnel through. A SQUID consists of tiny loops of superconductors employing Josephson junctions to achieve superposition: each electron moves simultaneously in both directions. Because the current is moving in two opposite directions, the electrons have the ability to perform as qubits (that theoretically could be used to enable quantum computing). SQUIDs have been used for a variety of testing purposes that demand extreme sensitivity, including engineering, medical, and geological equipment.

Both the low-field NMR and MRI are based on SQUID, which can avoid the drawbacks of high-field NMR and MRI such as susceptibility artifacts, the cost issue, the size and complexity of the high-field system and so on. The demand of the field homogeneity is not as strict as that of high-field NMR/MRI although the signal-to-noise ratio (SNR) is weak in low field NMR/MRI. Homogeneity of 1 part per $10^4$ in the magnetic field can reach a line width of 0.426 Hz in the NMR spectrum. Therefore, the construction of a low-field spectrometer of high spectral resolution is much easier than that of the high-field NMR/MRI.

Nuclear magnetic resonance imaging (MRI) is a clinical diagnostic tool which is based on the difference in longitudinal ($T_1^{-1}$) or transverse ($T_2^{-1}$) relaxation rates of protons in different tissues. In other words, it is important to study the change of spin-lattice relaxation time $T_1$, spin-spin relaxation time $T_2$ and effective relaxation time $T_2^*$ for medical diagnosis. However, it is still a little complicated and inconvenient to use so many parameters and make images for diagnosis.

Currently, the main method of distinguishing between normal tissue and tumor tissue depends on pathological analysis of specimen obtained from biopsy. Such examination demands high human resource as this requires professional pathologists and it takes time. Moreover, when the quantity of specimen is undersized, there is usually insufficient amount to conduct all the examinations. Therefore, pieces of specimen needs to be used for regular microscopic examination under H&E staining and many other immunohistochemical staining simultaneously for coming to diagnosis. Furthermore, the specimens are depleted and unable to be used in follow-up pathological examinations.

SUMMARY OF THE INVENTION

The present invention provides a method for rapid detecting tumor, comprising following steps of: (a) taking a small amount of patient tissue sample; (b) putting the patient tissue sample in non-magnetic container; (c) placing the patient tissue sample into a high-$T_c$ SQUID-based tabletop NMR system; (d) analyzing the patient tissue sample in microtesla magnetic fields; (e) getting $T_1^{-1}$ value of the patient tissue sample; (f) comparing the $T_1^{-1}$ value of the patient tissue sample with mean $T_1^{-1}$ value of normal tissue of the same kind tissue; (g) comparing the $T_1^{-1}$ value of the patient tissue sample with mean $T_1^{-1}$ value of tumor tissue of the same kind tissue; and (h) considering the patient to suffer from cancer when the $T_1^{-1}$ value of the patient tissue sample is close to mean $T_1^{-1}$ value of tumor tissue and to be a person without cancer when the $T_1^{-1}$ value of the patient tissue sample is close to mean $T_1^{-1}$ value of normal tissue.

DETAILED DESCRIPTION OF THE INVENTION

Figure 1A:
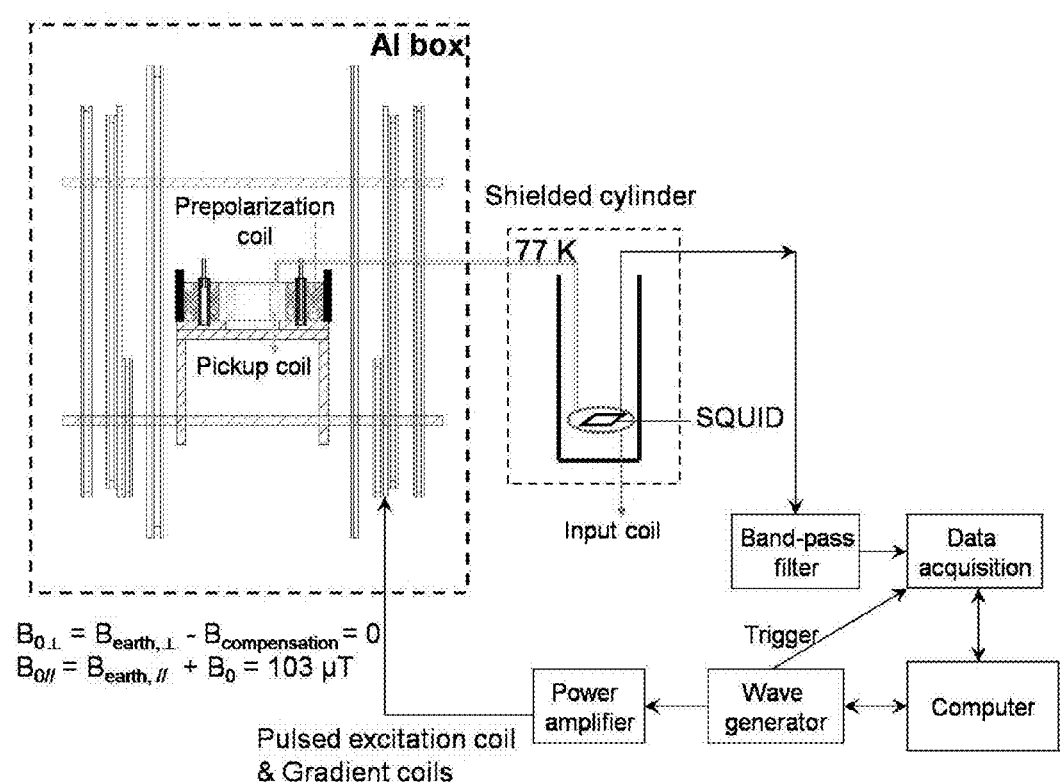
FIG. 1 shows 1A: schematic of a high-$T_c$ SQUID-based tabletop NMR system; 1B: the size of a sample container; 1C: the electro-magnetic protocol used; and 1D: the free induction decay signal.

This invention is about a method for rapid detecting tumor using a tabletop NMR system as described herein, and other aspects of the NMR systems are conventional and not described since they are well known in the art.

The present invention provides a method for rapid detecting tumor, comprising following steps of: (a) taking a small amount of patient tissue sample; (b) putting the patient tissue sample in non-magnetic container; (c) placing the patient tissue sample into a high-$T_c$ SQUID-based tabletop NMR system; (d) analyzing the patient tissue sample in microtesla magnetic fields; (e) getting $T_1^{-1}$ value of the patient tissue sample; (f) comparing the $T_1^{-1}$ value of the patient tissue sample with mean $T_1^{-1}$ value of normal tissue of the same kind tissue; (g) comparing the $T_1^{-1}$ value of the patient tissue sample with mean $T_1^{-1}$ value of tumor tissue of the same kind tissue; and (h) considering the patient to suffer from cancer when the $T_1^{-1}$ value of the patient tissue sample is close to mean $T_1^{-1}$ value of tumor tissue and to be a person without cancer when the $T_1^{-1}$ value of the patient tissue sample is close to mean $T_1^{-1}$ value of normal tissue.

In this invention, the patient tissue sample for analysis must be put in a non-magnetic container before detecting. In a preferable embodiment, the non-magnetic container is made of, but not limited to, PP, plastic, plastic wrap, or glass.

The term "tumor" used herein includes, but is not limited to, liver tumor, gastrointestinal cancer, leukemia, pituitary tumor, small cell lung cancer and thyroid cancer.

A preferable embodiment of this invention is for, but not limited to, rapid liver tumor detecting. In this embodiment, the tissue sample was patient liver tissue sample. To detect liver tumor by the high-$T_c$ SQUID-based tabletop NMR system, the least amount of patient liver tissue sample existed, say 1.05 gram in a preferable embodiment and 0.85 gram in a more preferable embodiment.

In the embodiment just mentioned, the $T_1^{-1}$ value of patient tissue sample is patient liver tissue sample $T_1^{-1}$ value, the mean $T_1^{-1}$ value of normal tissue is mean normal liver tissue $T_1^{-1}$ value, and the mean $T_1^{-1}$ value of tumor tissue is mean tumor liver tissue $T_1^{-1}$ value. The mean normal liver tissue $T_1^{-1}$ value in room temperature falls above a critical value, say 4.5 $s^{-1}$, in a preferable embodiment and between a critical value region, say 4.5-10 $s^{-1}$, in a more preferable embodiment; and the mean tumor liver tissue $T_1^{-1}$ value in room temperature falls below the critical value, say 4.5 $s^{-1}$, in a preferable embodiment and between a critical value region, say 3-4.5 $s^{-1}$, in a more preferable embodiment.

In the embodiment just mentioned, patient liver tissue sample must be unfrozen when analyzing. However, it can be measured once the sample temperature returns to room temperature, and after repeatedly frozen and defrosted, the $T_1^{-1}$ value of specimens will not change, means the specimens can be stored by refrigerating.

In this invention, the patient tissue sample can be preserved in formalin—the most common method of storing specimens. In a preferable embodiment, the patient tissue sample is the formalin processed patient liver tissue sample. The formalin will not significantly change the $T_1^{-1}$ value of sample, and after repeatedly frozen and defrosted, the $T_1^{-1}$ value of specimens will not change. Furthermore, the $T_1^{-1}$ value of specimens preserved in formalin in room temperature will not change, means the specimens can be stored in formalin.

In this invention, after the process for detecting tumor, the specimen will still be undamaged and can be used for other pathological analysis. This provides more possibility to exam undersized specimen.

To summarize this invention, we provide a rapid tumor detecting method that in room temperature, stable $T_1^{-1}$ value can be measured for tissues of certain sizes without introducing irrelevant effects from the materials of containers. In addition, the tissues only need to be stored in low temperature or be preserved in formalin to maintain their efficacy. The experimental measurements are not affect by the length of time the specimen are preserved. This method of examining and distinguishing normal and tumor tissues has the advantages of convenience, easiness of operation, stability, and other benefits. This invention provides a new direction of study in cancer pathology.

EXAMPLES

The examples below are non-limiting and are merely representative of various aspects and features of the present invention.

Example 1

Animal Tissue Sample Preparation 10 six-week-old male Wistar rats were chosen for the experiment. All rats were fed water that is mixed with 100 ppm diethylnitrosamine (DEN) for six weeks to induce hepatocellular carcinoma (HCC, liver tumor). All experiments were conducted after approval of the institutional animal care committee. After six weeks the rat livers should develop tumors that were 3-10 mm in diameter. The rats were then euthanized via $CO_2$ inhalation and the livers were harvested. Normal liver parenchyma and tumor tissues were stored separately in liquid nitrogen. Parts of specimens were stored in formalin solution and H & E stain was performed for prospective pathological studies. The pathologic diagnosis was made by two pathologists independently to identify liver and tumor tissues.

Example 2

High-$T_c$ SQUID-Based Tabletop NMR System Examination

We had had the measurement of NMR with the high-$T_c$ SQUID at magnetically shielded room (MSR). And the system now, different from the previous, was without at MSR. As shown in FIG. 1A, the system contained pick-up coil, pre-polarization coil, compensation coil and measurement coil, inside a four-layer aluminum shielding box to shield environmental noises. The measurement field generated from a three-coil pair could produce a field with $1/10^4$ homogeneity within a sample volume of 64 $cm^3$. The compensation coil compensated the vertical component of earth's magnetic field which was perpendicular to measurement field. The pick-up coil and the input coil formed a flux transformer via a tank circuit. The NMR signal of proton was inductively coupled to the SQUID magnetometer via the flux transformer. The SQUID detector and input coupling coil were placed inside a $Bi_2Sr_2Ca_2Cu_3O_y$, superconducting shielding can that was in magnetically shielded box.

Figure 1B:
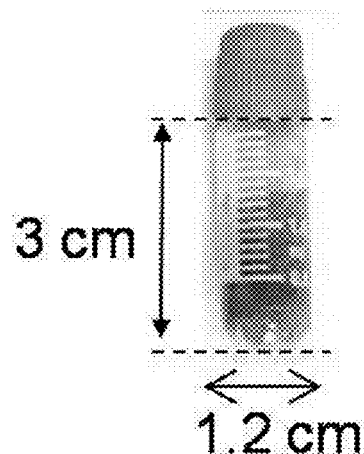
Figure 1C:
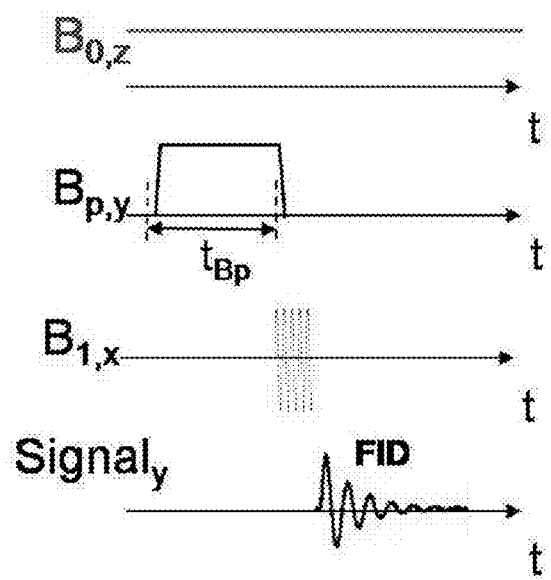

As shown in FIG. 1B, the tissue sample was put in a container about 3 cm in height and 1.2 cm in diameter and then put in the measuring site. The steps of measurement are stated following. In the experiment, the static field $B_0$ of 103 µT lasted along the z axis. $B_0$ was produced by the field generated from the coil and horizontal component of earth's magnetic field. The pre-polarization field $B_p$ of 100 mT was applied along the x axis. The strength of pre-polarization field was stronger than the static measuring field, resulting in the direction of nuclear spin magnetization of $^1H$ aligning along x axis. After a polarizing time, $t_{Bp}$, the pre-polarization field was turn off. For the presence of the static field $B_0$, the precession of the nuclear magnetization was varied the direction from x-axis to the z-axis. The spin magnetization of $^1H$ processed first inside the xy plane and finally, relaxed along the z axis. At the same time, the free induction decay (FID) signal of nuclear spin of $^1H$ was detected by the high-$T_c$ DC SQUID magnetometer via the flux transformer (FIG. 1C). The FID signal, which would be then recorded, passed through the band pass filter and amplifier. NMR signals, the intensity spectrum of sample under $B_0$, were obtained through the fast Fourier transformation.

Example 3

Fit the $T_1^{-1}$ Value

Variation of polarizing time, $t_{Bp}$, we gained the NMR signal corresponding with the variation. Each NMR intensity data $S(t_{Bp})$ were averaged 10 measurements. In general, the intensity $S(t_{Bp})$ can be described by the formula:

$$S(t_{Bp}) = S_0(1 - e^{-t_{Bp}/T_1}) \qquad (1)$$

Figure 1D:
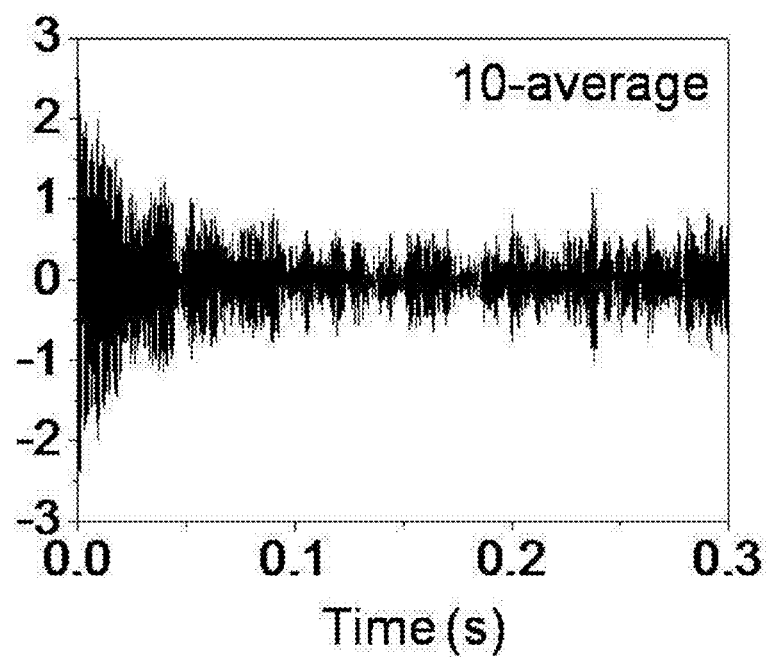

We can obtain $T_1^{-1}$ value from $S$-$t_{Bp}$ curve by the eq. (1) (FIG. 1D).

Example 4

Tumor Identification and Minimum Specimen Mass for Measurement

Figure 2A:
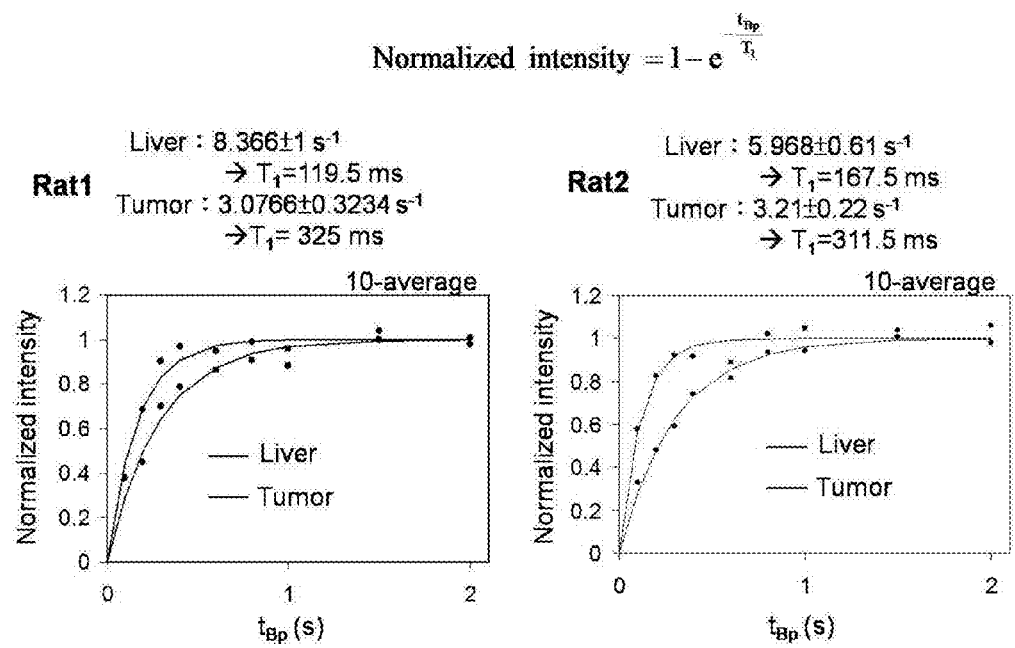
FIG. 2 shows 2A and 2B: the difference in $T_1^{-1}$ value between rat liver and tumor tissue; 2C and 2D: the least amount of sample mass of rat liver and tumor tissue needed for analysis; and 2E: the variation of $T_1^{-1}$ values in different weight of rat liver and tumor tissue.
Figure 2B:
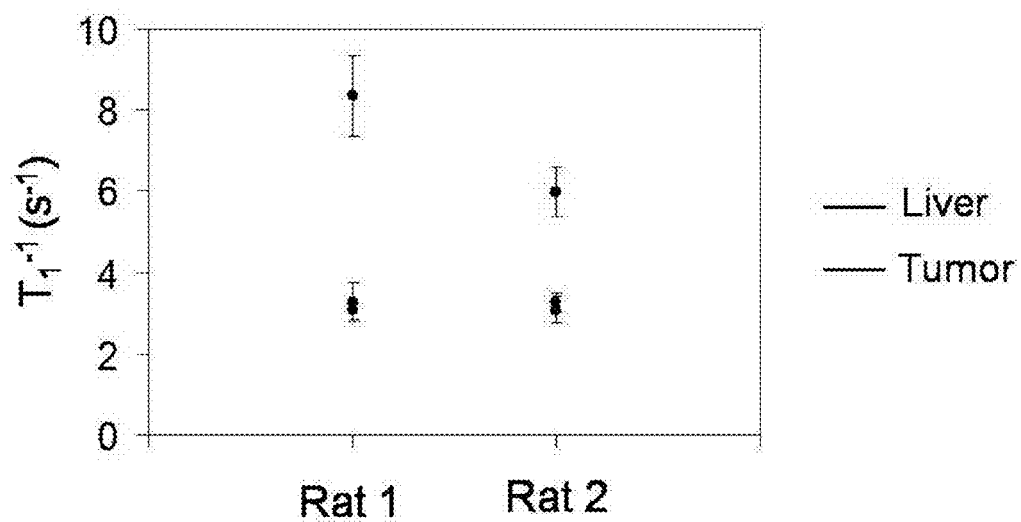

The both specimens of liver and tumor were divided into 5 pieces by different weights from 0.23 to 1.4 gram, and the $T_1^{-1}$ value of each sample was measured triplet. As shown in FIG. 2A, the $T_1^{-1}$ value of liver tissue fell above a certain value, e.g. 4.5 s$^{-1}$, and more exactly between a certain region, e.g. 4.5-10 s$^{-1}$; and the $T_1^{-1}$ value of cancer tissue fell below this critical value. More exactly, the $T_1^{-1}$ value of liver tissue fell between one certain region, e.g. 4.5-10 s$^{-1}$, and which of cancer tissue fell between the other certain region, e.g. 3-4.5 s$^{-1}$. These values suggested significant differences statistically between liver and tumor tissues ($p<0.05$) (FIG. 2B), and it demonstrated $T_1$ value's capability in distinguishing between liver and tumor tissue.

Figure 2C:
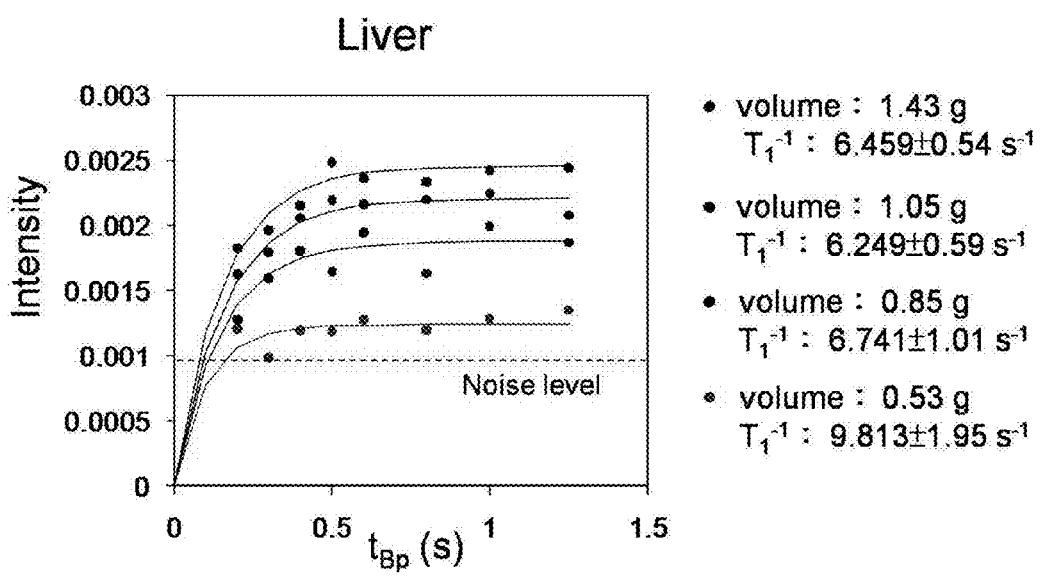
Figure 2D:
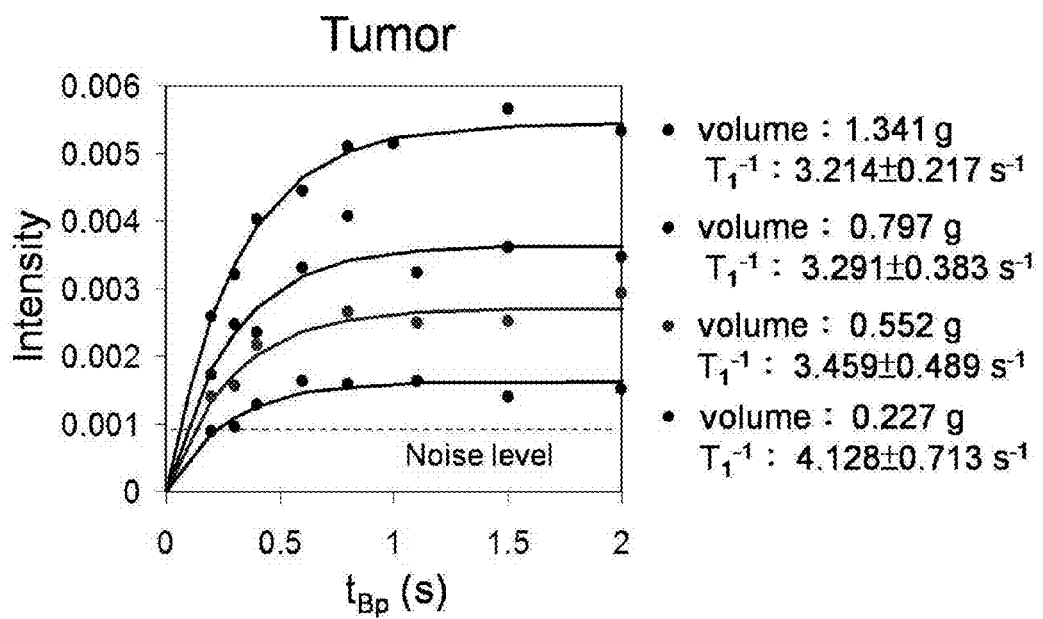
Figure 2E:
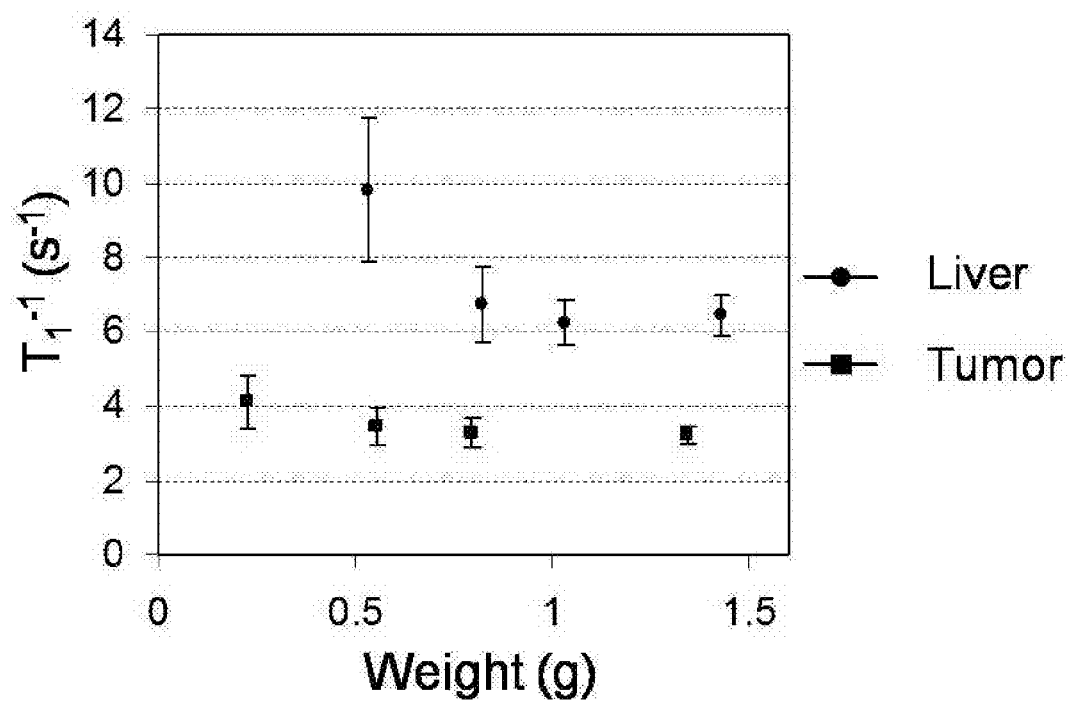

Then, specimens of different sizes were measured for the same examination. There exists the smallest specimen mass that could register a stable $T_1$ value, e.g. 0.85 gram in liver tissue (FIG. 2C), and 0.55 gram in tumor tissue (FIG. 2D). Specimens with weight greater than these values did not significantly affect the $T_1^{-1}$ value statistically (FIG. 2E), and the $T_1^{-1}$ value also fell above the critical value in liver tissue and fell below the critical value in tumor tissue.

Example 5

Container Material Test

To test weather different container materials affect the $T_1^{-1}$ value, each specimen was put in four commonly used containers made with different non-magnetic materials including PP, plastics, plastic wrap and glass, and the same evaluation was performed.

Figure 3A:
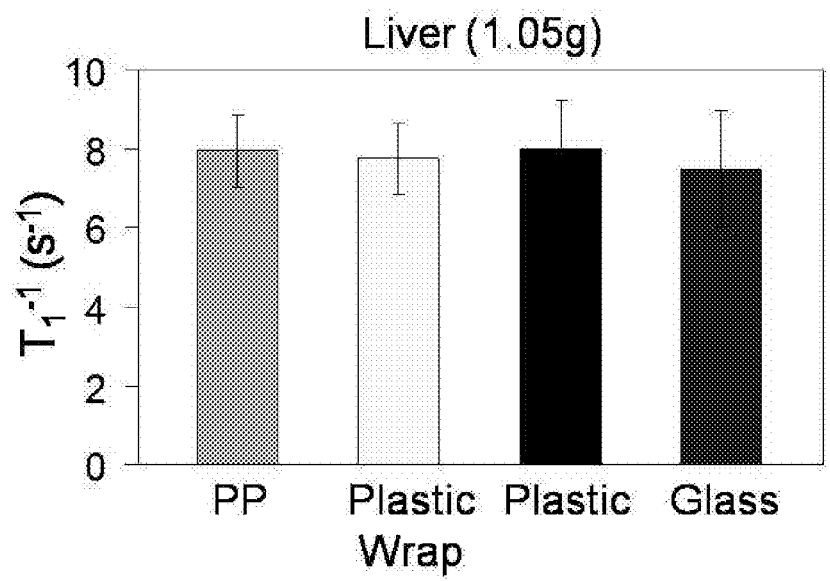
FIG. 3 shows that the $T_1^{-1}$ value of rat liver (3A) and liver tumor (3B) did not change when using containers made of different non-magnetic materials.
Figure 3B:
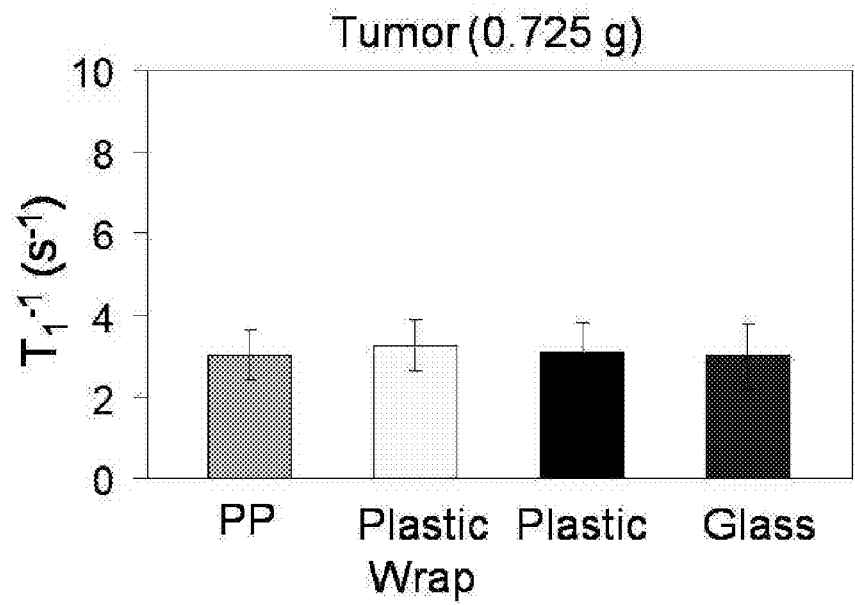

As shown in FIGS. 3A and 3B, the results yielded no statistical differences in $T_1^{-1}$ value in both liver tissue group (FIG. 3A) and tumor tissue group (FIG. 3B). Therefore, it concluded that $T_1^{-1}$ value was not influenced by materials of the containers that we generally used to store specimens.

Example 6

Repeatedly Freeze and Defrost Test

Each liver and tumor sample was divided equally into some different groups with the same weight: the group stored in room temperature, the group frozen in liquid nitrogen for examinations under frozen status, and the group frozen in liquid nitrogen, but defrosted in room temperature before performing any examinations and frozen again after the experiment. The $T_1^{-1}$ value of samples in every group was obtained on $1^{st}$, $2^{nd}$, $3^{rd}$, $4^{th}$, $5^{th}$, $6^{th}$, $7^{th}$, $30^{th}$, and $60^{th}$ day of experiment.

Figure 4A:
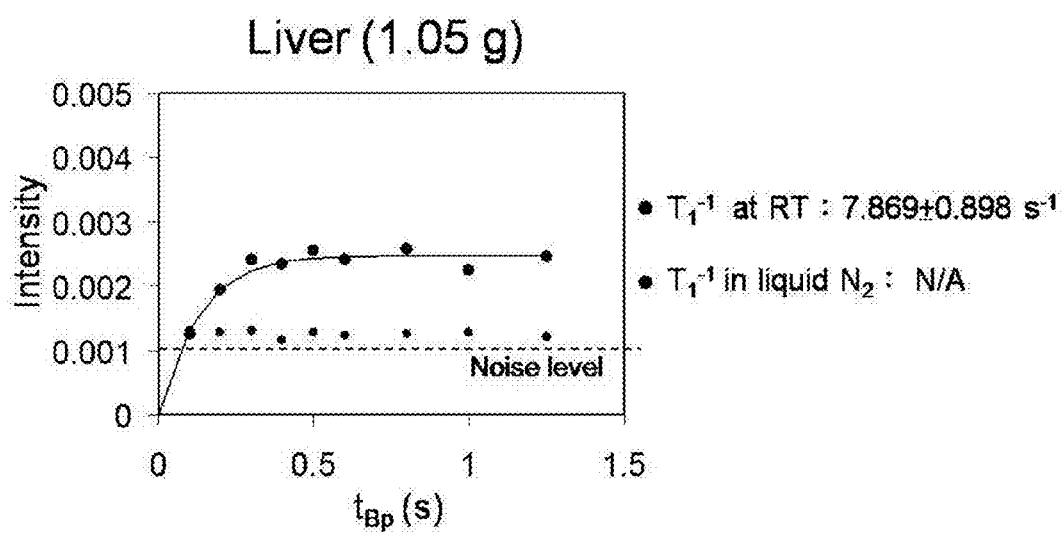
FIG. 4 shows that 4A and 4B: the $T_1^{-1}$ value of specimens could not be measured under frozen condition; and 4C: the $T_1^1$ value could be measured when returning to room temperature and was not different from which of fresh specimen.
Figure 4B:
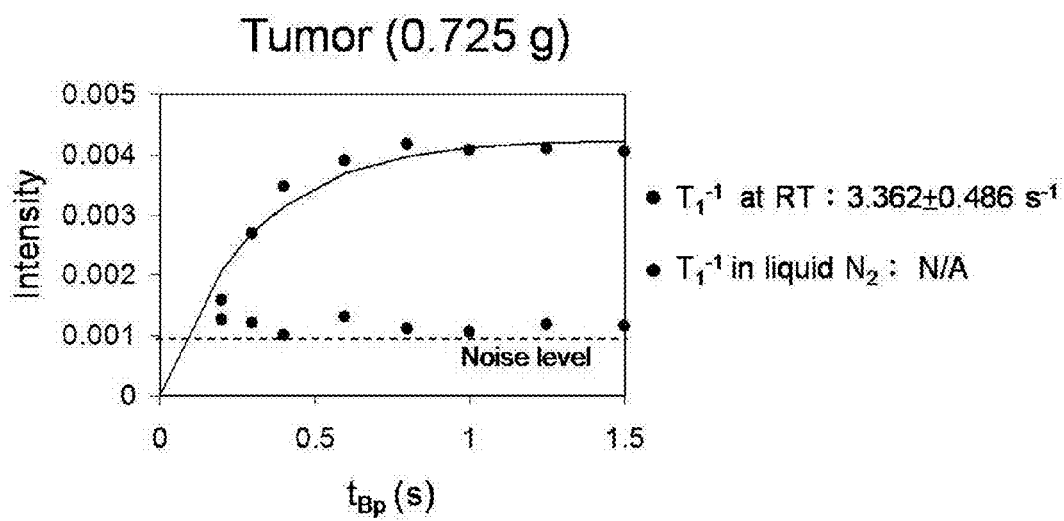
Figure 4C:
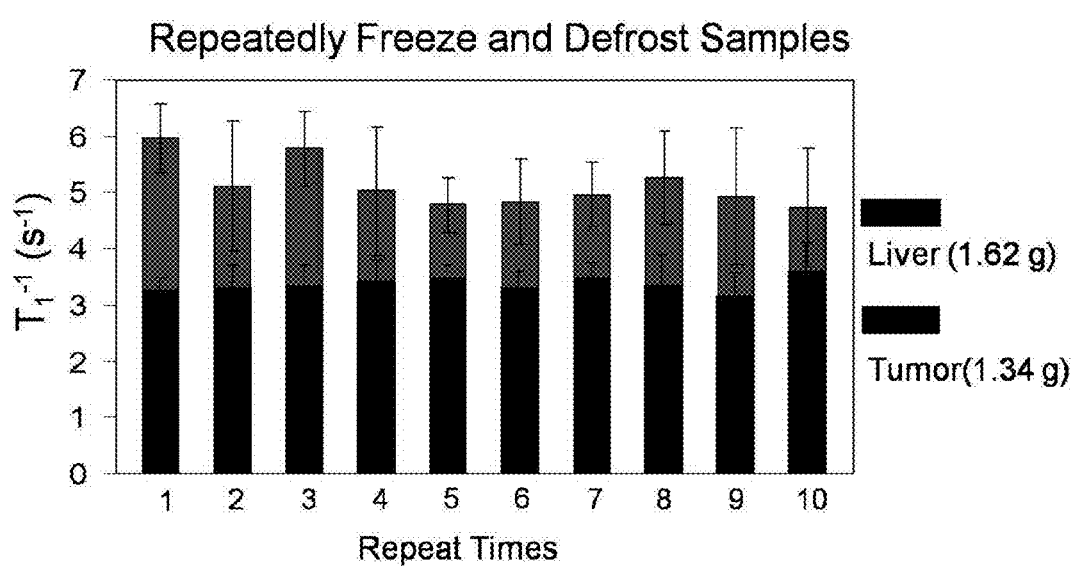
Figure 5A:
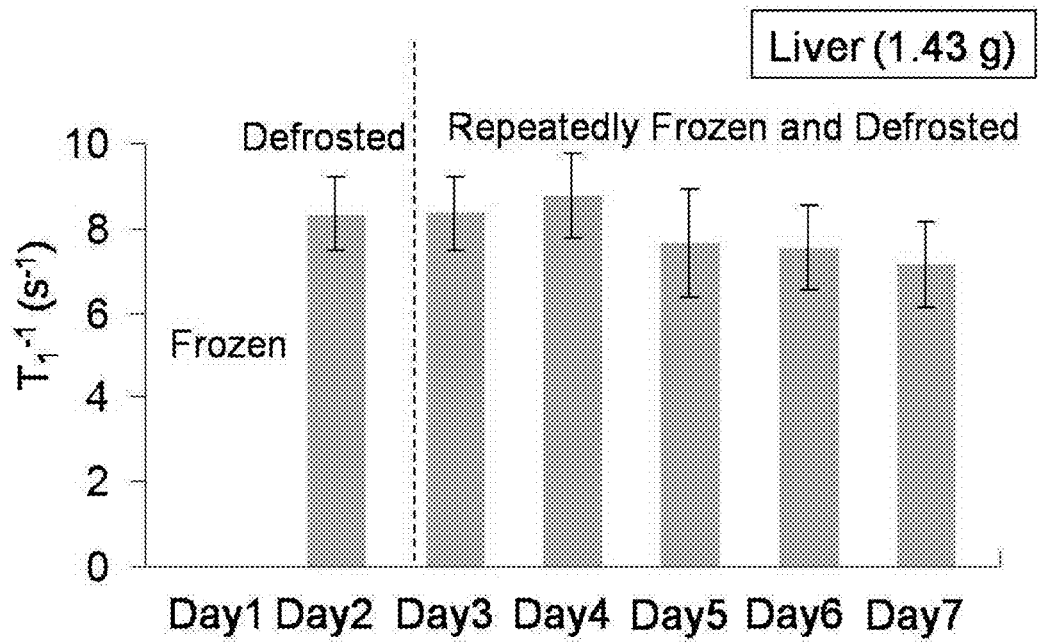
FIG. 5 shows that 5A and 5B: the $T_1^{-1}$ values did not vary significantly when the specimens were stored in liquid nitrogen for days; 5C: this consistency just mentioned was valid for at least thirty days; and 5D and 5E: the $T_1^{-1}$ value continued to decrease as time goes when specimen was kept under room temperature.
Figure 5B:
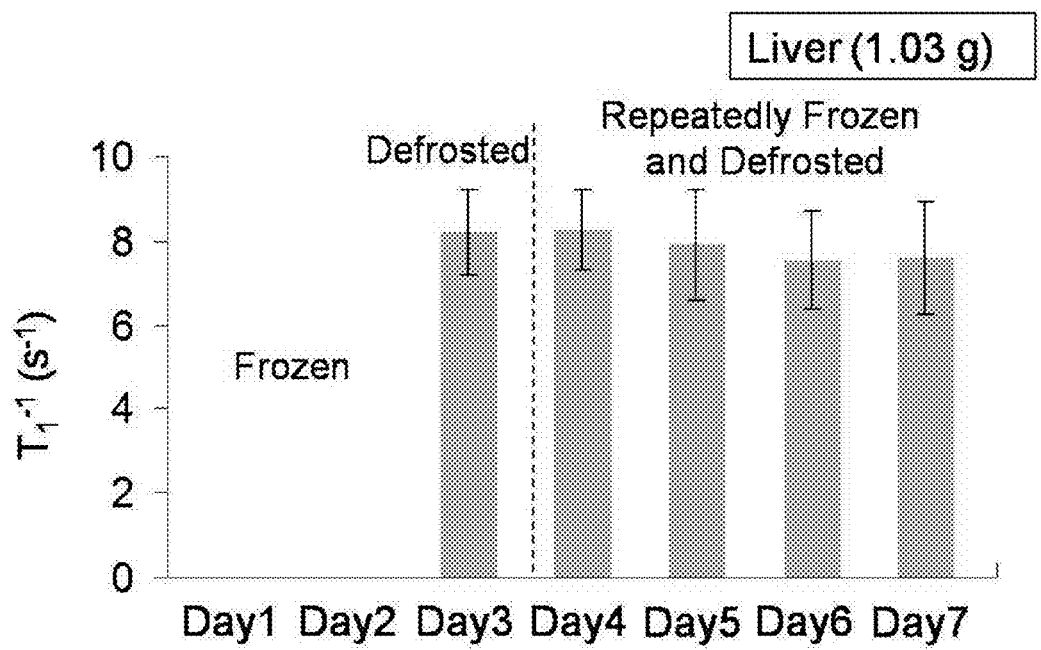
Figure 5C:
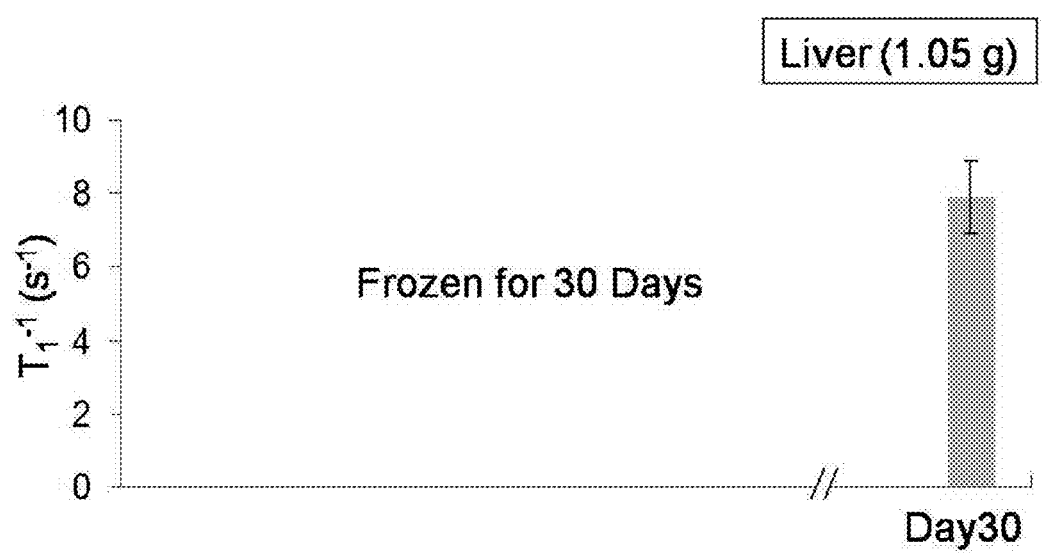

As shown in FIGS. 4A and 4B, $T_1^{-1}$ value of both liver tissue and tumor tissue could not be measured under frozen condition. However, the $T_1^{-1}$ value could be measured once the sample temperature returned to room temperature, and there was no statistical difference in $T_1^{-1}$ value between fresh and repeatedly frozen and defrosted specimens (FIG. 4C). Even when the specimen was stored in liquid nitrogen for over a long period of time the result was still consistent, and the $T_1^{-1}$ value did not vary significantly (FIGS. 5A and 5B). This consistency was valid for at least thirty days (FIG. 5C).

Figure 5D:
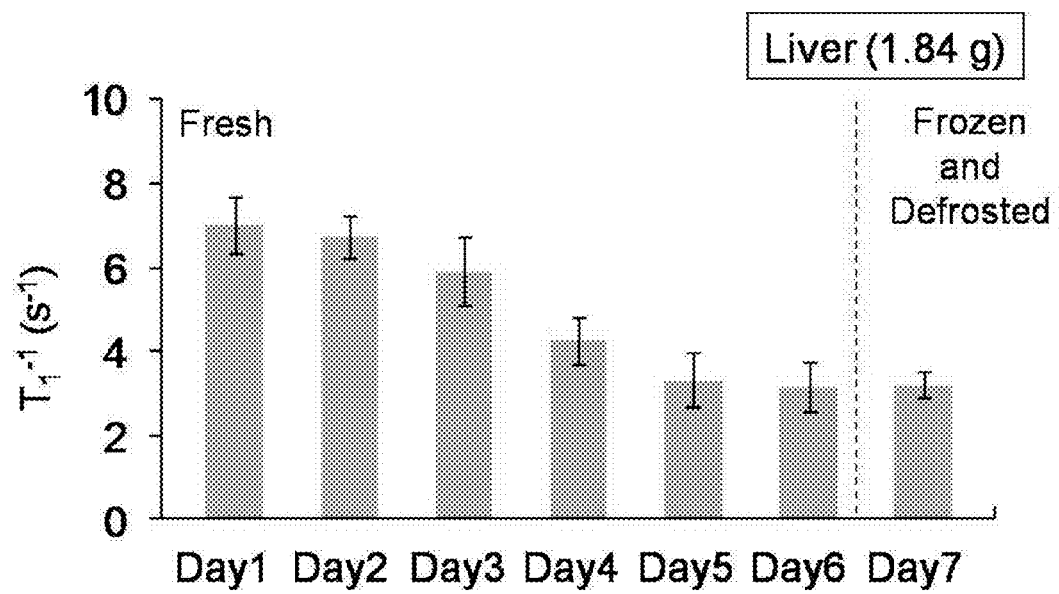
Figure 5E:
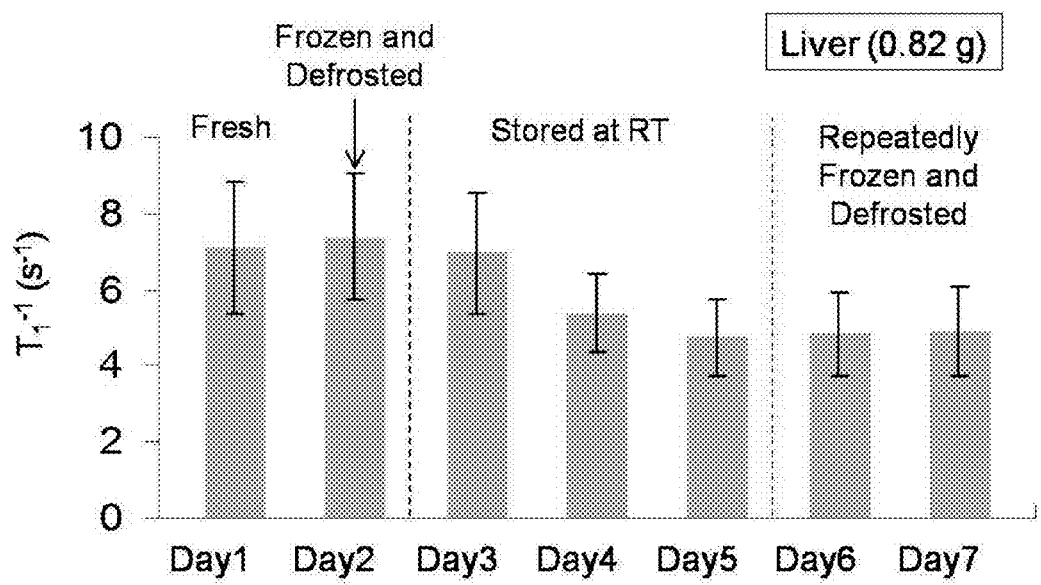

Moreover, as shown in FIGS. 5D and 5E, if specimen was kept under room temperature, the value would continue to decrease as time goes on and the result would become unreliable.

Example 7

Formalin Preservation

In the end, the formalin test was performed. All liver and tumor samples with the same weight were preserved in formalin, and the $T_1^{-1}$ value of samples in every group was obtained on $1^{st}$, $2^{nd}$, $3^{rd}$, $4^{th}$, $5^{th}$, $6^{th}$, $7^{th}$, $30^{th}$, and $60^{th}$ day of experiment.

Figure 6A:
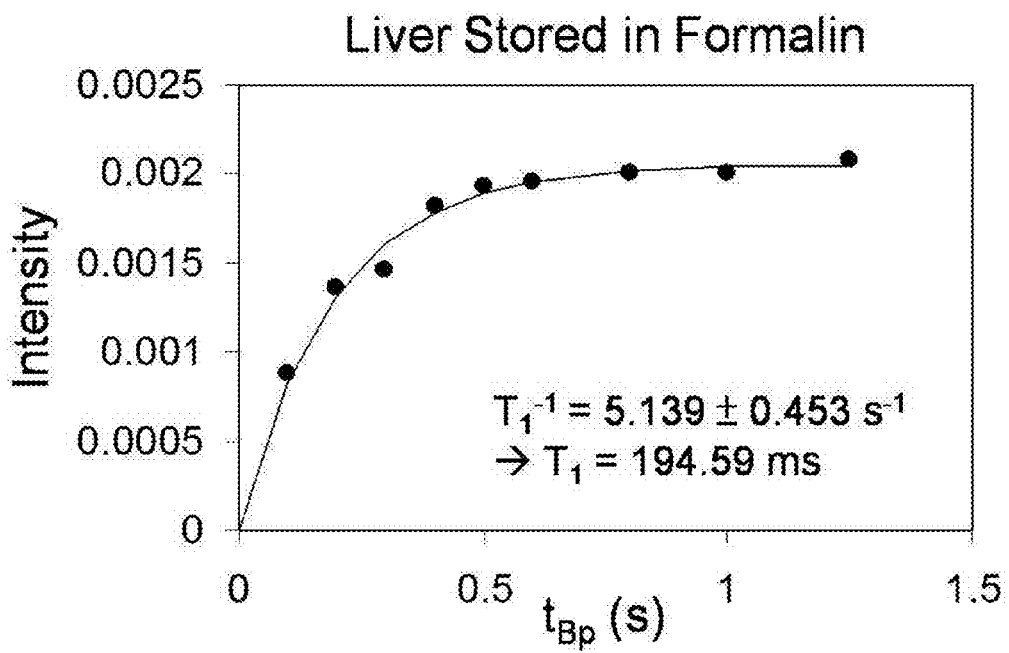
FIG. 6 shows no statistical difference in $T_1^{-1}$ value between fresh and formalin preserved specimens in both liver group (6A) and tumor group (6B).
Figure 6B:
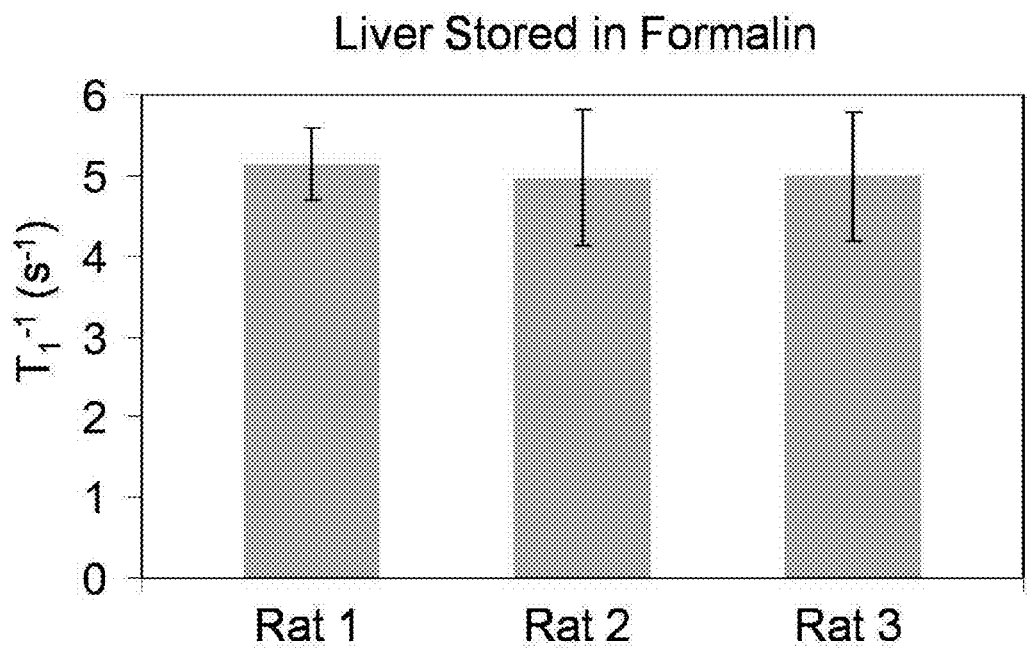
Figure 7:
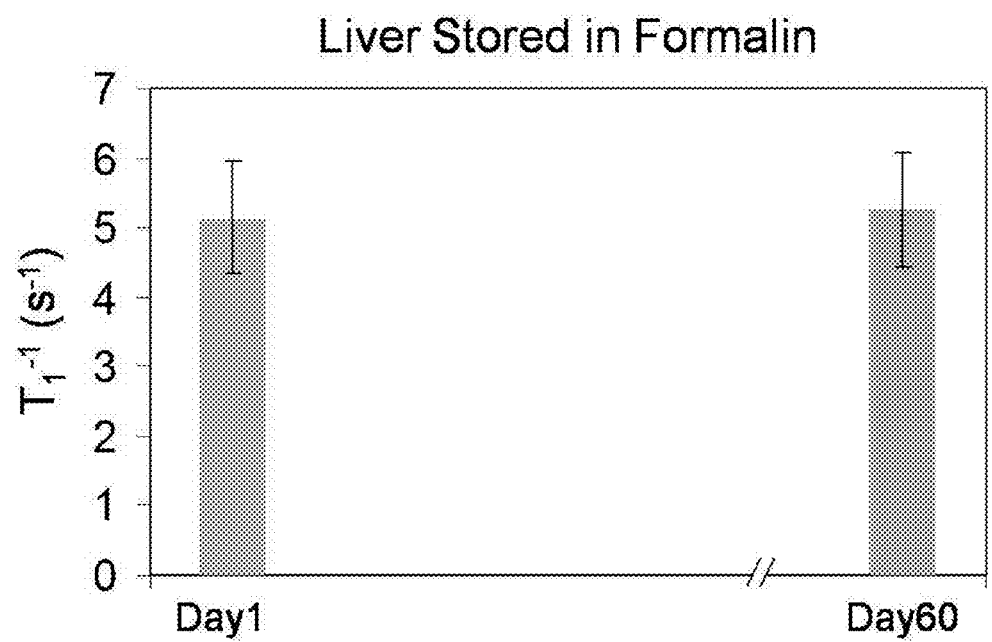
FIG. 7 shows that the $T_1^{-1}$ value did not vary significantly when the specimen was stored in formalin for sixty days.

As shown in FIGS. 6A and 6B, there was no statistical difference in $T_1^{-1}$ value between fresh and formalin preserved specimens. Furthermore, the $T_1^{-1}$ value did not vary significantly after sixty days (FIG. 7). These data told that this invention can also detect the $T_1^{-1}$ value of specimens which are preserved in formalin—the most common method of storing specimens—under the aforementioned conditions.

What is claimed is:

1. A method for rapid detecting tumor comprising following steps of:
   (a) taking a small amount of patient tissue sample;
   (b) putting the patient tissue sample in non-magnetic container;
   (c) placing the patient tissue sample into a high-$T_c$ SQUID-based tabletop NMR system;
   (d) analyzing the patient tissue sample in microtesla magnetic fields;
   (e) getting $T_1^{-1}$ value of the patient tissue sample;
   (f) comparing the $T_1^{-1}$ value of the patient tissue sample with mean $T_1^{-1}$ value of normal tissue of the same kind tissue;
   (g) comparing the $T_1^{-1}$ value of the patient tissue sample with mean $T_1^{-1}$ value of tumor tissue of the same kind tissue; and
   (h) considering the patient to suffer from cancer when the $T_1^{-1}$ value of the patient tissue sample is close to mean $T_1^{-1}$ value of tumor tissue and to be a person without cancer when the $T_1^{-1}$ value of the patient tissue sample is close to mean $T_1^{-1}$ value of normal tissue.

2. The method of claim 1, wherein the tissue sample is from liver.

3. The method of claim 2, wherein the amount of the patient liver tissue sample is greater than a minimum weight.

4. The method of claim 3, wherein the minimum weight is 0.85-1.05 gram.

5. The method of claim 1, wherein the container is made of PP, plastic, plastic wrap, or glass.

6. The method of claim 1, wherein the $T_1^{-1}$ value of the patient tissue sample is patient liver tissue sample $T_1^{-1}$ value.

7. The method of claim 1, wherein the mean $T_1^{-1}$ value of the normal tissue is mean normal liver tissue $T_1^{-1}$ value.

8. The method of claim 7, wherein the mean normal liver tissue $T_1^{-1}$ value falls above a critical value in room temperature.

9. The method of claim 8, wherein the critical value is 4.5 s$^{-1}$.

10. The method of claim 7, wherein the mean normal liver tissue $T_1^{-1}$ value falls between a critical region in room temperature.

11. The method of claim 10, wherein the critical region is 4.5-10 s$^{-1}$.

12. The method of claim 1, wherein the mean $T_1^{-1}$ value of the tumor tissue is mean tumor liver tissue $T_1^{-1}$ value.

13. The method of claim 12, wherein the mean tumor liver tissue $T_1^{-1}$ value falls below a certain critical value in room temperature.

14. The method of claim 13, wherein the critical value is 4.5 s$^{-1}$.

15. The method of claim 12, wherein the mean tumor liver tissue $T_1^{-1}$ value falls between a critical region in room temperature.

16. The method of claim 15, wherein the critical region is 3-4.5 $s^{-1}$.

17. The method of claim 1, wherein the patient tissue sample is unfrozen when analyzing.

18. The method of claim 1, wherein the patient tissue sample is preserved by refrigerating before analyzing.

19. The method of claim 1, wherein the patient tissue sample is preserved in formalin when analyzing.

20. The method of claim 1, wherein the patient tissue sample is preserved in formalin before analyzing.

* * * * *